United States Patent [19]
Sriram et al.

[11] Patent Number: 5,854,285
[45] Date of Patent: Dec. 29, 1998

[54] PROTEIN KINASE INHIBITOR

[75] Inventors: Subramaniam Sriram; John Bright, both of Nashville, Tenn.; Bishwajit Nag, Fremont; Somesh D. Sharma, Los Altos, both of Calif.

[73] Assignee: Natpro, Inc., Union City, Calif.

[21] Appl. No.: 825,662

[22] Filed: Apr. 3, 1997

[51] Int. Cl.[6] .......................... A61K 31/21; A61K 31/26; A61K 31/275

[52] U.S. Cl. .......................... 514/514; 514/523; 514/525

[58] Field of Search ........................ 514/515, 514, 514/525, 523

[56] References Cited

U.S. PATENT DOCUMENTS

| | | |
|---|---|---|
| 5,196,446 | 3/1993 | Levitzki et al. . |
| 5,217,999 | 6/1993 | Levitzki et al. . |
| 5,266,594 | 11/1993 | Dawson et al. . |
| 5,302,606 | 4/1994 | Spada et al. . |
| 5,385,915 | 1/1995 | Buxbaum et al. . |

FOREIGN PATENT DOCUMENTS

| | | |
|---|---|---|
| WO 95/14464 | 6/1995 | WIPO . |
| WO 95/21613 | 8/1995 | WIPO . |

OTHER PUBLICATIONS

Galea, E., et al. (1995) "Differential suppression of glial nitric oxide synthase induction by structurally related tyrosine kinase inhibitors," *Neuroscience Lett.* 200:195–198.

Gazit et al., (1989) *J. Med. Chem.,* 32:2344–2352.

Gazit et al., (1991) *J. Med. Chem.,* 34:1896–1907.

Gazit et al., (1993) *J. Med. Chem.* 36:3556–3564.

Katsumi, I., et al. (1985) *Chem Pharm. Bull.* "Studies on Styrene Derivatives.II. Synthesis and Antiinflammatory Activity of 3,5-Di-*tert*-butyl-4-hydroxystyrenes," 34:1619–1627.

Kenatharan, M., et al. (1996) *Brit. J. of Pharm.* "Analysis of the signal transduction in the induction of nitric oxide synthase by lipoteichoic acid in macrophages." 117:1163–1170.

Levitzki, A. (1992) "Typhstins: tyosine kinase blockers as novel antiproliferative agent and dissector of signal transduction," *The FASEB Journal* 6:3275–3282.

Novogrodsky, A., et al. (1994) "Prevention of Lipopolysaccharide–Induced Lethal Toxicity by Tyrosine Kinase Inhibitors," *Science* 264:1319–1322.

Shiraishi, T., et al. (1987) "Specific Inhibitors of Tyrosine–Specific Protein Kinases. I. Synthesis and Inhibitory Activities of α–Cyanocinnamamides," *Chem. Pharm. Bull.* 36:974–981.

Tan, C.M., et al. (1995) "Oxidant Stress Enhances Adenylyl Cyclease Activation," *Circulation Research* 77:710–717.

Vanickin, A., et al. (1995) "Late Administration of a Lipophilic Tyrosine Kinases Inhibitor Prevents Lipopolysaccharide and *Escherichia coli*–Induced Lethal Toxicity," *J. Infectious Diseases* 173:927–933.

LC Laboratories Catalog Pages, pp.217, 218, 220.

*Primary Examiner*—Keith D. MacMillan
*Attorney, Agent, or Firm*—Fish & Richardson P.C.

[57] ABSTRACT

A compound of the formula I

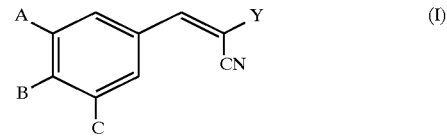

wherein A and C are independently H, alkyl of 1–6 carbon atoms, hydroxy, or alkoxy of 1–6 carbon atoms;

B is hydroxy or alkoxy of 1–6 carbon atoms; and

Y is cyano,

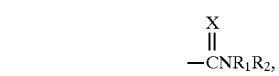

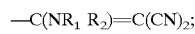

wherein X=O or S, and $R_1$ and $R_2$ are independently H, benzyl, —CH(CH$_3$), C$_6$H$_5$ —(CH$_2$)$_n$ C$_6$H$_6$, phenyl; —CO$_2$R;

n=2–4; R is lower alkyl of 1–6 carbon atoms is used for treating inflammation and immunological diseases.

7 Claims, 3 Drawing Sheets

PROTEIN KINASE INHIBITOR

FIELD OF THE INVENTION

The present invention relates to the method of use of styrene derivatives to treat inflammation and immunological diseases.

BACKGROUND OF THE INVENTION

The present invention is based on the crucial role played by signaling pathways in affecting the function of cytokines. Cytokines are molecules secreted by immune cells and are important in mediating immune responses. Cytokines effect their functions at the site of secretion or at distant sites. Cytokines initiate their responses by binding to their respective receptors. This receptor-ligand interaction induces a signal and leads to the transcription of new genes that change the functional capacity of the target cell. Thus the effect of cytokines may result in the secretion of other cytokines, altered cellular function, cell division or differentiation. In most immune cells (T, B and macrophages) cytokine receptors themselves act as protein tyrosine kinases that are phosphorylated upon ligation of the receptor or are closely linked to phosphotyrosine kinases (PTK's).

Inhibitors of PTK function are known, such as querestin, the first one which was isolated. Querestin was found to inhibit not only PTK's but other enzymes such as cAMP dependent kinase, protein kinase C (PKC) and ATP requiring enzymes. Other naturally occurring compounds such as erbastatin, herbamycin and levandestin affect predominantly the function of PTK's and have been termed tyrphostins. Most tyrphostins are 100–1000 fold more potent in inhibiting PTK's than PKA, PKC or other calcium dependent kinases. So far the role of tyrphostins has focused on their potential application in neoplastic diseases. A recent therapeutic test of tyrphostins has been in the treatment of acute lymphoblastic leukemia, in which a known JAK2 kinase inhibitor was shown to inhibit the proliferation of leukemic cells without affecting mitogen-induced T cell proliferation.

The present invention is directed to treatment of immunological diseases or inflammation. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNFα all of which are potent pro-inflammatory molecules and also provide help for T cells. In addition, activation of macrophages results in the induction of enzymes, such as cyclooxygenase II (COX II), nitric oxide (NO) and other free radicals capable of damaging normal cells. Many factors activate macrophages, including bacterial products, superantigens and interferon gamma (IFNγ). It is believed that PTK's and other undefined cellular kinases are involved in the activation process.

Macrophages take up and break down antigens into small fragments. These fragments then associated with the major histocompatibility complex II (MHC II). This complex of antigen fragments and MHC II is recognized by the T cell receptor. In association with appropriate co-stimulatory signals this receptor-ligand interaction leads to the activation and proliferation of T cells. Depending on the route of administration of antigen, their dose and the conditions under which macrophages are activated, the immune response can result in either B cell help and antibody production or on the development of cell mediated response. Since macrophages are sentinel to the development of an immune response, agents that modify their function specifically their cytokine secretion profile are likely to determine the direction and potency of the immune response.

SUMMARY OF THE INVENTION

This invention is directed to a method of treating immunological diseases or inflammation with compounds of formula I shown below. The compounds inhibit the secretion of pro-inflammatory cytokines and thus prevent the development or inhibit established inflammatory responses.

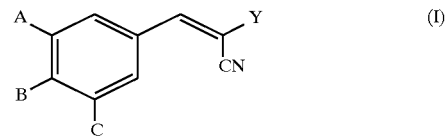

wherein A and C are independently H, alkyl of 1–6 carbon atoms, hydroxy, or alkoxy of 1–6 carbon atoms;

B is hydroxy or alkoxy of 1–6 carbon atoms; and

Y is cyano,

or

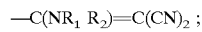

wherein X=O or S, and $R_1$ and $R_2$ are independently H, benzyl, —CH(CH$_3$), C$_6$H$_5$

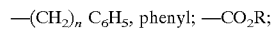

n=2–4; R is lower alkyl of 1–6 carbon atoms.

DESCRIPTION OF THE PREFERRED EMBODIMENTS

As used herein the term tyrphostins is intended to denote a family of organic molecules that have the effect of inhibiting protein tyrosine kinases.

The immune diseases include those mediated by signaling pathways linked to pro-inflammatory cytokines, such as, multiple sclerosis, rheumatoid arthritis, contact and atopic dermatitis.

The compounds used in accordance with the present invention are those of the formula I. The alkyl and alkoxy groups in formula I may be linear or branched. A preferred class of compounds is that in which A and C are independently hydrogen or hydroxy and Y is cyano. A particularly preferred compound within this class is the compound in which B is methoxy and A and C are both hydrogen.

The compounds of the formula I are obtained by synthetic methods known in the art. See Gazit et al., *J. Med. Chem.*, 1991, 34:1896–1907; 1989, 32:2344–2352; 1993, 36:3556–3564; and U.S. Pat. No. 5,217,999, issued Jun. 8, 1993 to Levitski et al., all of which are incorporated by reference herein in their entirety.

The compounds may be administered to the host suffering from inflammation or a immunological disease using any convenient administration technique, where such techniques include intravenous, intradermal, intramuscular, subcutaneous, oral, and the like. The dosage delivered to the host will necessarily depend on the route by which the active compound is administered, but will generally range from about 1 to 500 mg/70 kg human body weight/day.

The compounds of this invention may be used in formulations using acceptable pharmaceutical vehicles for enteral, or parenteral, administration, such as, for example, water, alcohol, gelatin, gum arable, lactose, amylase, magnesium stearate, talc, vegetable oils, polyalkylene glycol, and the like. The compounds can be formulated in solid form, e.g., as tablets, capsules, drages and suppositories, or in the liquid form, e.g., solutions, suspensions and emulsions. The preparations may also be delivered transdermally or by topical application.

The following examples are presented by way of illustration, and are not intended to limit the invention in any way.

EXAMPLE 1

Tyrphostin A1 (Formula I: A and C are H, B is methoxy, Y is CN) is as efficient as A10 (A is H, B is —$NO_2$, C is OH, Y is —CN) and B42 (A and B are OH, C is H, Y is C(O)$NHCH_2C_6H_6$) in inhibiting nitric oxide and IL 12 Secretion by splenic macrophages.

Tyrphostin A1 has been used as a negative control for tyrphostins because of it weak effect on inhibition of epidermal growth factor receptor (EGFR) kinase activity. Tyrphostin A10 has been shown to be protective in septic shock and B42 is effective in preventing the growth of leukemic cells in acute lymphoblastic leukemia.

Figure 1A:
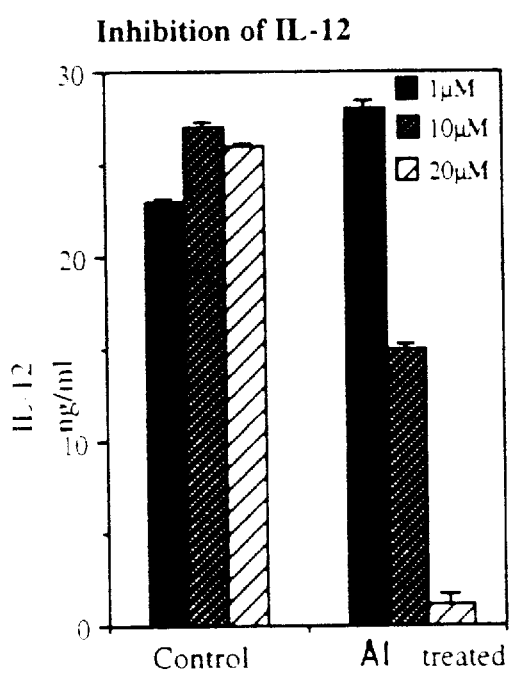
FIGS. 1A and 1B show the IL-12 and nitric oxide inhibition of tyrphostin 1A described in Example 1.
Figure 1B:
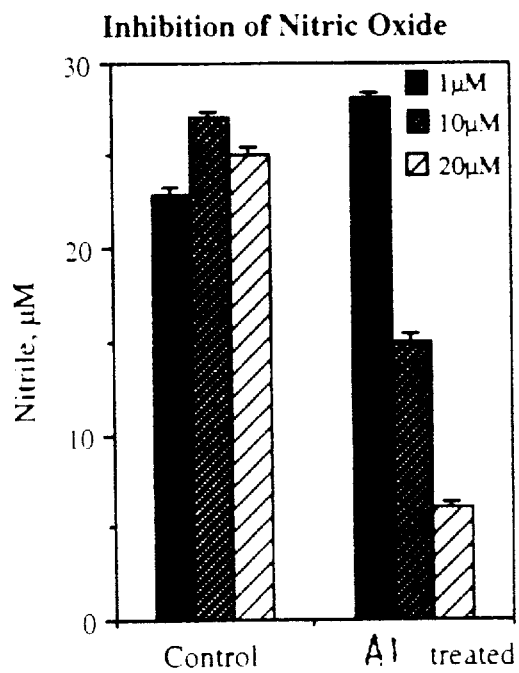

The effects of these three tyrphostins on the secretion of pro-inflammatory cytokines from macrophages were compared. Mouse splenic macrophages were stimulated with 5 ugh/ml lipopolysaccharide (LPS) and treated with varying doses of tyrphostins. The cells were cultured for 72 hr and the amount of IL 12 and nitric oxide was measured. Tyrphostins A1, A10 and B42 all inhibited IL 12 production. In general, tyrphostin A1 was more potent (FIG. 1A) than the other tyrphostins in inhibiting IL 12 secretion. Similar results were obtained with respect to nitric oxide levels, with tyrphostin A1 (FIG. 1B) showing good results.

Figure 2A:
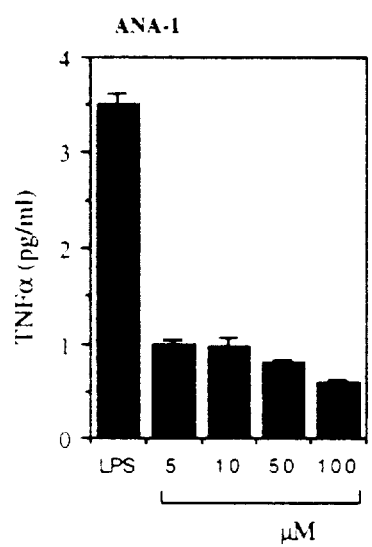
FIGS. 2A, 2B and 2C show the TNFα production by tyrphostin 1A in three macrophage cell populations.
Figure 2B:
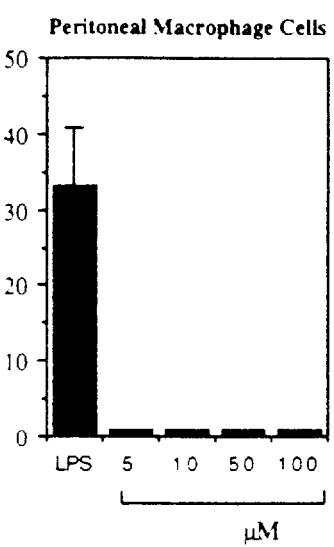
Figure 2C:
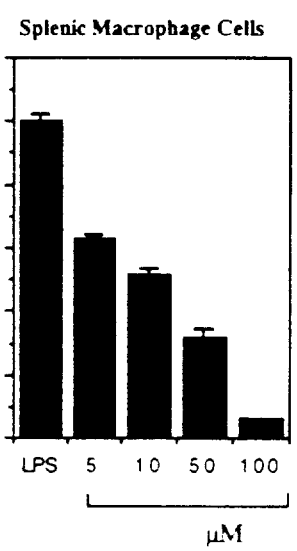

The effect of tyrphostin A1 on inhibition of TNFα was examined in vitro in a cultured macrophage cell line, peritoneal macrophages and splenic macrophages. Cells were cultured with 5 ug/ml LPS in the presence of varying concentrations of tyrphostin A1. Following 24 hr incubation, cell supernatants were harvested and the amount of TNFα was measured using a biological assay. Tyrphostin A1 inhibits TNFα secretion in three different populations (ANA-1, FIG. 2A; peritoneal macrophage cells, FIG. 2B; splenic macrophages cells, FIG. 2C) of macrophages. FIGS. 2A and 2C show that the inhibition occurs in a dose dependent fashion.

Tyrphostin A1 was also tested for its ability to modulate the function of cyclooxygenase (COX II), an enzyme found in cells in inflammatory lesions. Hence, down regulation of this enzyme will be highly beneficial in damping inflammation. The induction of COX II in murine peritoneal macrophages activated with LPS was inhibited by tyrphostin A1.

The restrictive effects of tyrphostin A1 on proinflammatory cytokines was confirmed by examining the enhanced expression of class II MHC molecules induced by IFNγ. Tyrphostin A1 at concentrations at which it inhibits secretion of pro-inflammatory cytokines had no effect on enhancement of class II MHC levels by IFNγ (Table I).

TABLE I

| Stimulation | % MHC Class II + Cells |
| --- | --- |
| None | 26.6% |
| IFNγ | 58.2% |
| IFNγ + Tyrphostin A1 (1 μM) | 64.1% |
| IFNγ + Tyrphostin Al (1 μM) | 60.4% |

The selectivity of tyrphostins for macrophages was further confirmed by testing their effects on T cell proliferation induced by either IL 12 or IL 2. Mitogen stimulated mouse splenic T cells were cultured in serum free medium for 24 hr. The cells were then stimulated with either 1 U/ml IL 2 or 10 U/ml IL 12 in the presence or absence of tyrphostin A1. Tyrphostin B42 inhibited T cell proliferation when cultured with IL 2 or IL 12. Tyrphostin A1 and A10 did not show any significant inhibition.

EXAMPLE 2

Tyrphostin A1 is tested on experimental allergic encephalomyelitis (EAE) in mice.

The condition EAE is an animal model which mimics human multiple sclerosis. Therefore, the clinical efficacy of tyrphostin A1 was tested in mice suffering from EAE. Female SJL/J mice were randomly assigned into 2 groups of 5 animals each. EAE was induced by subcutaneous immunization with mouse spinal cord homogenate (800 ug/animal) in complete Freund's adjuvant on days 0 and 7. One group of animals was treated with 5 mg/kg tyrphostin A1 subcutaneously on days 1, 3, 5, 7 and 9 after immunization. Animals were observed and graded for the clinical signs every day. The severity of the disease was scored as: 1, loss of tail tone; 2' hind limb weakness; 3, hind limb paralysis; 4, moribund and 5, death.

Figure 3:
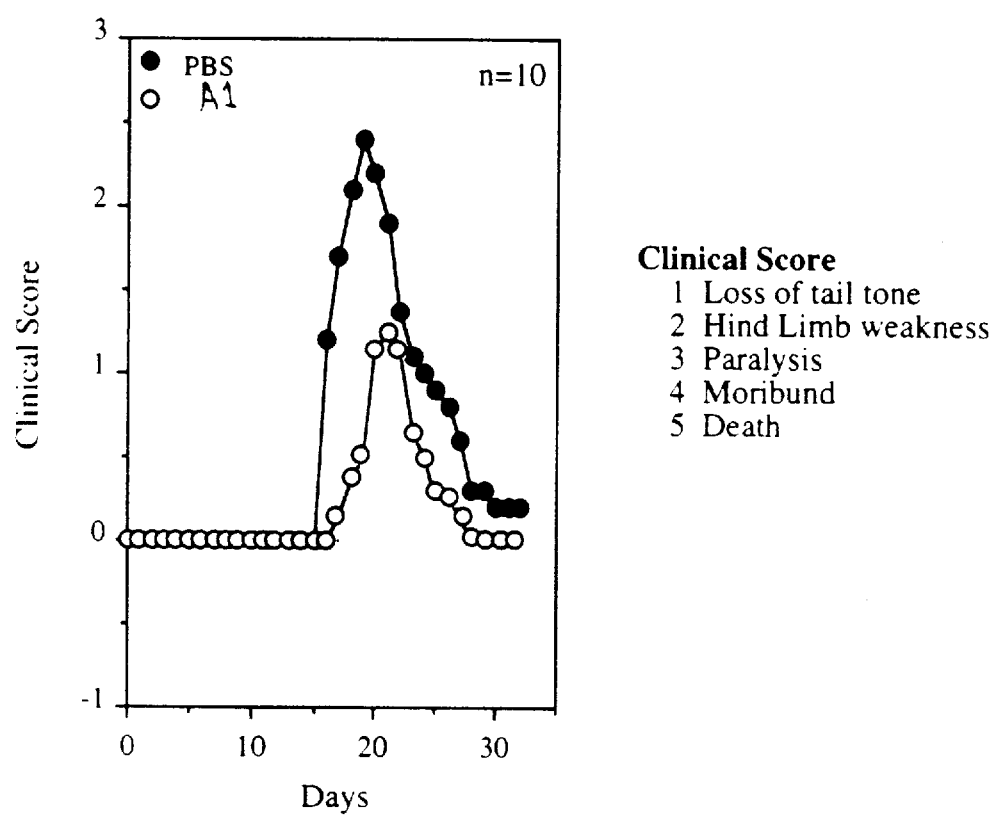
FIG. 3 shows the prevention of EAE in mice by tyrphostin 1A.

FIG. 3 shows the summary of data on subcutaneous administration of tyrphostin A1 indicating a decrease in the clinical severity of EAE. Animals in the control group had a peak mean severity of 2.5 at day 20. This was reduced to 1.25 at day 20 by tyrphostin A1.

The data demonstrate the utility of tyrphostin A1 in blocking pro-inflammatory cytokines and in treating a prototype inflammatory disease.

What is claimed is:

1. A method for treating inflammation in a patient suffering from an inflammatory condition comprising the step of administering a therapeutically effective amount of a compound of the formula:

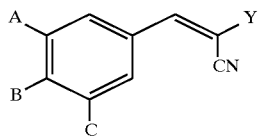 (I)

wherein A and C are H,
B is methoxy; and
Y is cyano,

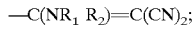

wherein X=O or S, and $R_1$ and $R_2$ are independently H, benzyl, —CH(CH$_3$), C$_6$H$_5$ —(CH$_2$)$_n$ C$_6$H$_5$, phenyl;

n=2–4; R is lower alkyl of 1–6 carbon atoms.

2. A method according to claim 1 wherein Y is CN.

3. The method of claim 1 wherein said compound is administered in a dose range from 1 mg/day to 500 mg/day.

4. The method of claim 1 wherein said compound is administered orally, parenterally, transdermally or topically.

5. A method for treating an immunological disease in a patient afflicted with said disease comprising the step step of administering a therapeutically effective amount of a compound of the formula:

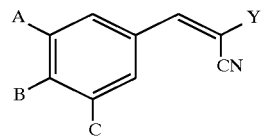 (I)

wherein A and C are H,
B is methoxy; and
Y is cyano,

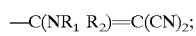

wherein X=O or S, and $R_1$ and $R_2$ are independently H, benzyl, —CH(CH$_3$), C$_6$H$_5$ —(CH$_2$)$_n$C$_6$H$_5$, phenyl;

n=2–4; R is lower alkyl of 1–6 carbon atoms.

6. The method according to claim 5 wherein said disease is multiple sclerosis.

7. The method according to claim 5 wherein Y is CN.

* * * * *

UNITED STATES PATENT AND TRADEMARK OFFICE
CERTIFICATE OF CORRECTION

PATENT NO. : 5,854,285

DATED : December 29, 1998

INVENTOR(S) : Sriram

It is certified that error appears in the above-identified patent and that said Letters Patent is hereby corrected as shown below:

Title page, OTHER PUBLICATIONS, please insert the following:

Chemical Abstracts AN 1992:420509, Salari, corresponding to CA 2012634, 9/20/91.

Chemical Abstracts AN 1995:782006, Levitzki et al., corresponding to PCT WO9514464.

Signed and Sealed this

Twenty-first Day of September, 1999

Attest:

Q. TODD DICKINSON

*Attesting Officer*         *Acting Commissioner of Patents and Trademarks*